United States Patent
Onuki et al.

(10) Patent No.: US 12,241,676 B2
(45) Date of Patent: Mar. 4, 2025

(54) COOLING BOX AND ANALYSIS DEVICE

(71) Applicant: Hitachi High-Tech Corporation, Tokyo (JP)

(72) Inventors: Kazutoshi Onuki, Tokyo (JP); Akimasa Osaka, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 174 days.

(21) Appl. No.: 18/023,484

(22) PCT Filed: Sep. 4, 2020

(86) PCT No.: PCT/JP2020/033587
§ 371 (c)(1),
(2) Date: Feb. 27, 2023

(87) PCT Pub. No.: WO2022/049722
PCT Pub. Date: Mar. 10, 2022

(65) Prior Publication Data
US 2023/0304728 A1 Sep. 28, 2023

(51) Int. Cl.
*F25D 25/02* (2006.01)
*G01N 35/10* (2006.01)
*G01N 35/00* (2006.01)

(52) U.S. Cl.
CPC ....... *F25D 25/025* (2013.01); *G01N 35/1002* (2013.01); *G01N 2035/00435* (2013.01)

(58) Field of Classification Search
CPC .............. F25D 25/025; G01N 35/1002; G01N 35/1095; G01N 35/00; G01N 2035/00435; C12M 1/00
See application file for complete search history.

(56) References Cited

U.S. PATENT DOCUMENTS

2005/0173399 A1   8/2005   Yoshidome et al.
2018/0321269 A1   11/2018  Takeuchi et al.

FOREIGN PATENT DOCUMENTS

| CN | 102754522 A | * | 10/2012 | ............ F25D 31/005 |
| JP | 2005221081 A | * | 8/2005 | .............. F24C 15/02 |

(Continued)

OTHER PUBLICATIONS

International Search Report (PCT/ISA/210) issued in PCT Application No. PCT/JP2020/033587 dated Nov. 2, 2020 with English translation (four (4) pages).

(Continued)

*Primary Examiner* — Emmanuel E Duke
(74) *Attorney, Agent, or Firm* — Crowell & Moring LLP (57) ABSTRACT

This cooling box for storing reagents and the like in a cold state, becomes a cantilever structure where, when a slide rail is disposed outside a cooling space, an installation part is held only by a drawer door. When a heavy article is placed, the installation part is deformed and broken. This cooing box includes a sliding member holder provided with sliding members each including a compression coil spring, which is an elastic body inside a heat insulating box body. When a reagent container is installed in the installation part and drawn out, the installation part and the sliding members slide in contact with each other. When a load exceeding the weight of an installed article is applied to the installation part, the installation part and the sliding member holder come into surface contact with each other. Thus, deformation and breakage of the installation part can be prevented.

10 Claims, 12 Drawing Sheets

(56) References Cited

FOREIGN PATENT DOCUMENTS

| | | |
|---|---|---|
| JP | 2017-32209 A | 2/2017 |
| JP | 2019-45122 A | 3/2019 |
| WO | WO 2017/086128 A1 | 5/2017 |

OTHER PUBLICATIONS

Japanese-language Written Opinion (PCT/ISA/237) issued in PCT Application No. PCT/JP2020/033587 dated Nov. 2, 2020 (three (3) pages).

* cited by examiner

COOLING BOX AND ANALYSIS DEVICE

TECHNICAL FIELD

The present invention relates to an analysis device, and more particularly, to a cooling box for storing a reagent in a cold state in the analysis device.

BACKGROUND ART

A next-generation sequencer is widely used as a device for analyzing nucleic acid such as deoxyribonucleic acid (DNA). Measurement performed by the next-generation sequencer is performed using a flow cell (sample substrate) in which a large number of microreaction fields are fixed. The next-generation sequencer irradiates the reaction fields on the flow cell with excitation light via an objective lens, and detects fluorescence from the reaction fields by a two-dimensional sensor such as a charge coupled device (CCD) camera or a complementary metal oxide semiconductor (CMOS) camera.

Accordingly, base information can be obtained as a fluorescence image. In this way, a chemical reaction is caused on the microreaction fields fixed to the flow cell, and fluorescence observation is performed, whereby a base sequence of a target DNA can be analyzed.

For a fluorescence reaction, various kinds of reagents are used. Since these reagents deteriorate in quality at room temperature, stable analysis can be performed by refrigeration storage not only before these reagents are mounted on the device but also after these reagents are mounted on the device. Therefore, the device includes a reagent cooling box for storing and refrigerating the reagents. A door part of the reagent cooling box mounted on such an analysis device is considered to be of an open-door type or a drawer type, and in view of usability, the drawer type is often used in order to avoid scattering of the reagents into the device when the reagents are dropped by mistake.

The reagent cooling box mounted on the analysis device has the same structure as a general food refrigerator, and there are several different points.

A first point is that shortening of the cooling time is required. The food refrigerator is always cooled and used by continuous energization, whereas it is common to turn on a power supply of the analysis device when the analysis device is used to reduce power consumption. It takes a certain period of time to cool inside of the reagent cooling box from the room temperature to a refrigerating temperature. However, since the time is the waiting time of a user, it is required to shorten the time as much as possible.

A second point is that a load other than the weight of a bridged article is applied to a drawer. In order to prevent evaporation, a method of minimizing evaporation by providing a film on an upper surface of a reagent container, breaking through a film by an aspiration nozzle immediately before the reagent is aspirated, and aspirating the reagent as it is may be adopted. In this case, the load is applied to the drawer when the aspiration nozzle breaks through the film. In a case of a configuration in which the same number of aspiration nozzles as the number of reagent containers are formed in order to prevent contamination, the load breaking through the film increases by the number of aspiration nozzles.

CITATION LIST

Patent Literature

PTL 1: JP2019-45122A
PTL 2: JP2005-221081A

SUMMARY OF INVENTION

Technical Problem

In general, in a food refrigerator including a drawer structure using a slide rail, the slide rail is disposed in a cooling space (for example, see PTL 1). However, when the shortening of the cooling time described above is considered, the slide rail does not need to be cooled normally, and thus cooling efficiency is reduced accordingly. It is desirable to minimize a heat capacity other than an object to be cooled, and it is considered to provide the slide rail outside the cooling space as a measure.

A device described in PTL 2 is a device that performs heating instead of cooling, and although a purpose is different, a slide rail is disposed outdoor. However, the device becomes a cantilever structure where, since the slide rail is simply disposed outdoor, a bridging part is held only by a drawer door, and the drawer door is used as a fixed end. It is preferable that a bridged article is light in weight. However, when a heavy article is placed or the load for breaking through the film described above is applied, a deflection of the bridging part occurs at a position away from the drawer door due to a moment, and deformation and breakage of the bridging part occur.

The invention is made in view of the above problems, and an object of the invention is to provide a drawer type cooling box that prevents deformation and breakage of a bridging part even when a load is applied to the bridging part in a structure in which a slide rail is disposed outside a cooling space, and an analysis device using the same.

Solution to Problem

In order to achieve the above object, the invention provides a cooling box including: a heat insulating box body configured to keep a temperature inside the heat insulating box body; a cooler configured to supply cold air to inside of the heat insulating box body; a bridging part configured to bridge a container containing a liquid to be kept in temperature to be accommodated in the heat insulating box body; a drawer door including the bridging part; and a slide rail that is movable in a front-rear direction, in which the heat insulating box body includes a nozzle insertion hole in an upper part thereof and a sliding member holder provided with a sliding member configured to slide with the bridging part, when the container is bridged on the bridging part and drawn out, the bridging part and the sliding member slide in contact with each other, and the bridging part is accommodated in the heat insulating box body, and when a load exceeding a weight of a bridged article is applied to the bridging part, the bridging part and the sliding member holder come into surface contact with each other.

In order to achieve the above object, the invention provides an analysis device including: a cooling box including the heat insulating box body configured to keep a temperature inside the heat insulating box body, a cooler configured to cool inside of the heat insulating box body, a bridging part configured to bridge a container containing a liquid to be kept in temperature to be accommodated in the heat insulating box body, a drawer door including the bridging part and a slide rail that is movable in a front-rear direction, in which, the heat insulating box body includes a nozzle insertion hole in an upper part thereof and a sliding member holder provided with a sliding member configured to slide with the bridging part, when the container is bridged on the bridging part and drawn out, the bridging part and the sliding member slide in contact with each other, and the bridging part is accommodated in the heat insulating box body, and when a load exceeding a weight of a bridged article is applied to the bridging part, the bridging part and the sliding member holder come into surface contact with each other; a lifting-lowering mechanism configured to lift and lower an aspiration nozzle to the container in the heat insulating box body; a liquid feeding mechanism configured to feed the liquid to be kept in temperature aspirated by the aspiration nozzle; a flow cell provided between the container and the liquid feeding mechanism; a temperature adjusting mechanism configured to adjust a temperature of the flow cell; and a detection unit configured to detect inside of the flow cell.

Advantageous Effects of Invention

In the structure in which the slide rail is disposed outside the cooling space, even when the load exceeding the weight of the bridged article is applied to the bridging part in a state in which the drawer is closed, an effect of preventing the deformation and the breakage is exhibited. Further features of the invention will become apparent based on the description of the invention and the accompanying drawings. Problems, configurations, and effects other than those described above will become apparent according to the following description of examples.

DESCRIPTION OF EMBODIMENTS

Hereinafter, various embodiments of the invention will be described in detail with reference to drawings. Although the drawings show examples according to principles in the invention, the drawings are shown for a purpose of understanding the invention, and are not to be used for limiting interpretation of the invention.

First Embodiment

FIGS. 1 to 6 show a cooling box 100 according to a first embodiment. As shown in FIGS. 1 to 6, the cooling box 100 according to the first embodiment includes a heat insulating box body 101, a cooler 500, a bridging part 102, a drawer door 103, and slide rails 104.

The heat insulating box body 101 has a function of thermally insulating cold air inside the heat insulating box body and outside air outside the heat insulating box body. Specifically, the heat insulating box body can be formed by combining a resin material and a foamed polystyrene having a low thermal conductivity or a vacuum insulation material. An upper part thereof is formed with a nozzle insertion hole 105 which is accessed by an aspiration nozzle 401 for conveying a reagent. Since the same number of aspiration nozzles 401 as the number of reagent containers 301 are formed in order to prevent contamination, the same number of the nozzle insertion holes 105 as the number of the reagent containers 301 are also formed.

Figure 1:
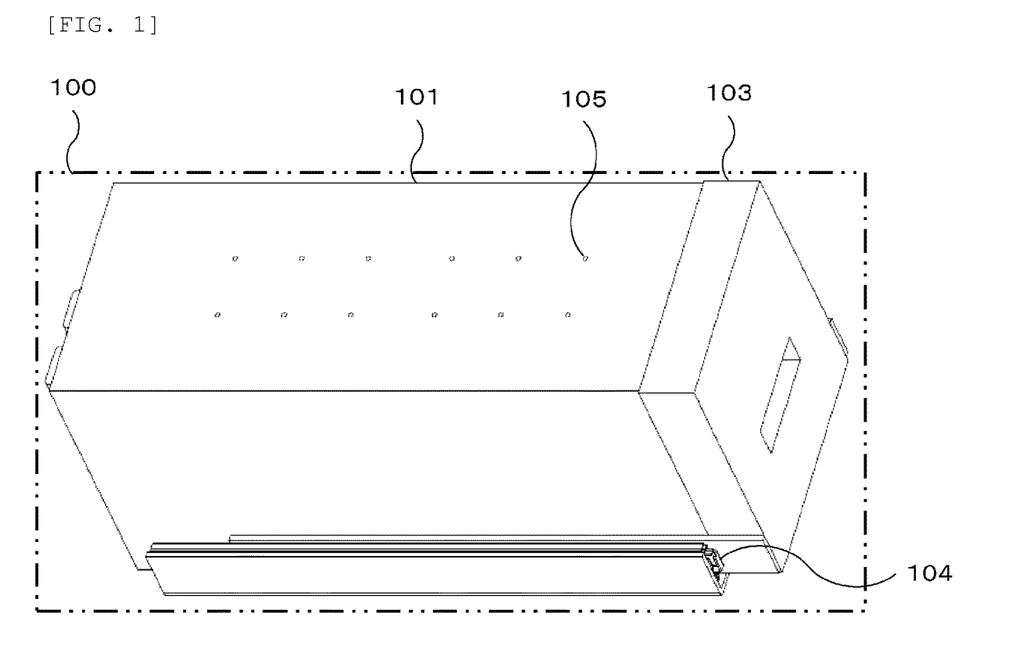
FIG. 1 is an external perspective view of a cooling box when a drawer is closed according to a first embodiment.
Figure 2:
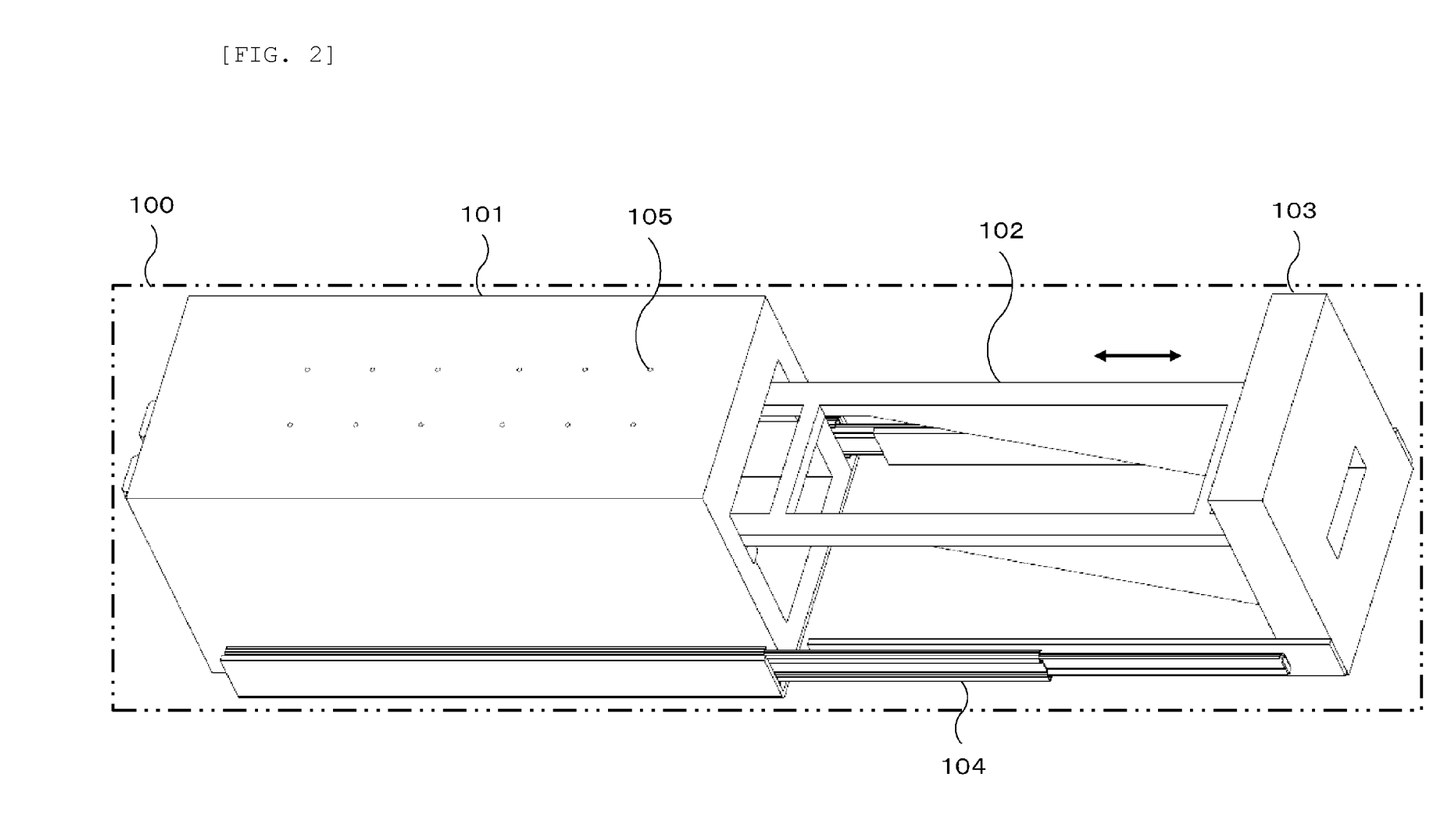
FIG. 2 is an external perspective view of the cooling box when the drawer is open according to the first embodiment.
Figure 3:
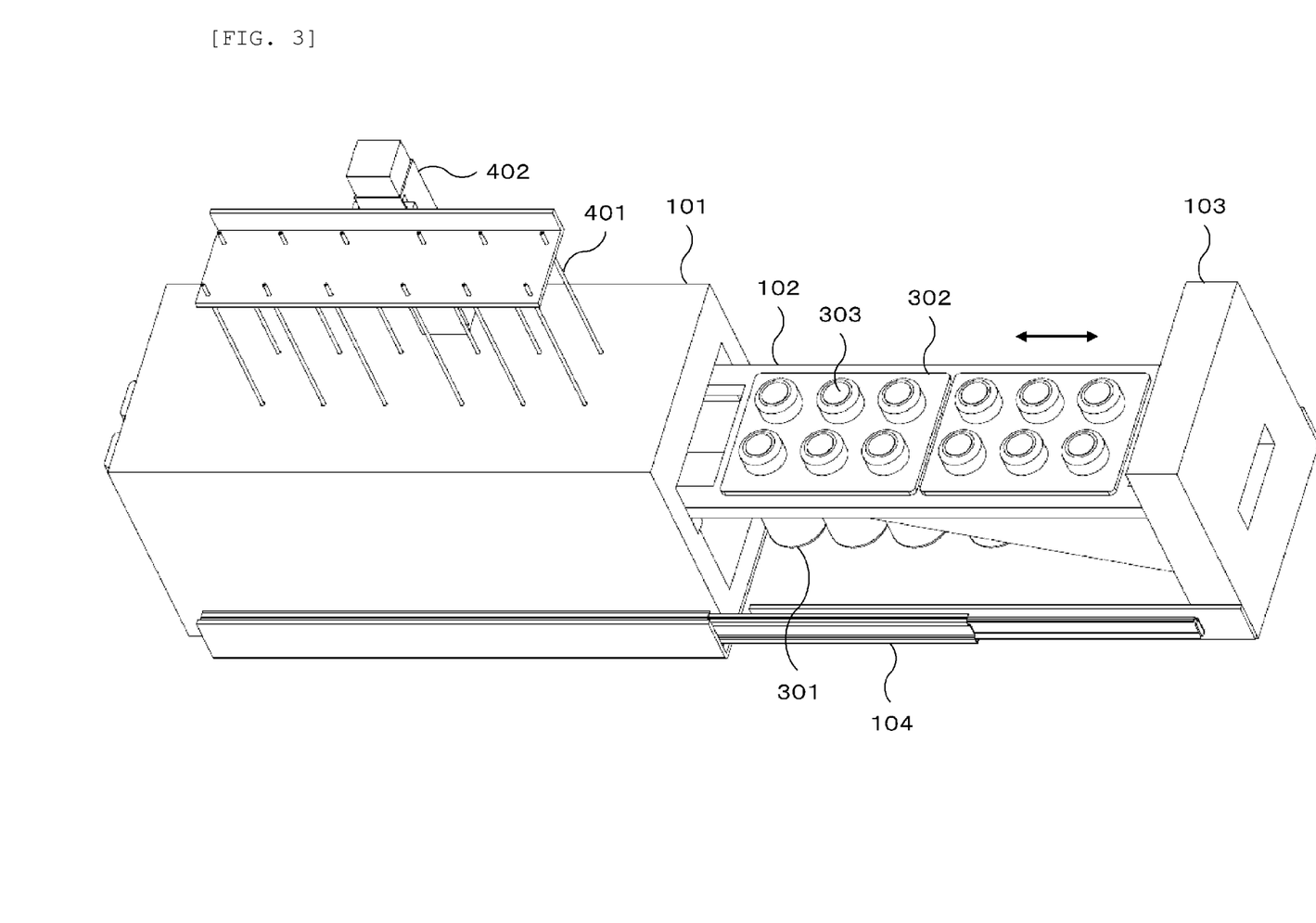
FIG. 3 is an external perspective view of the cooling box and peripheral components according to the first embodiment.
Figure 4:
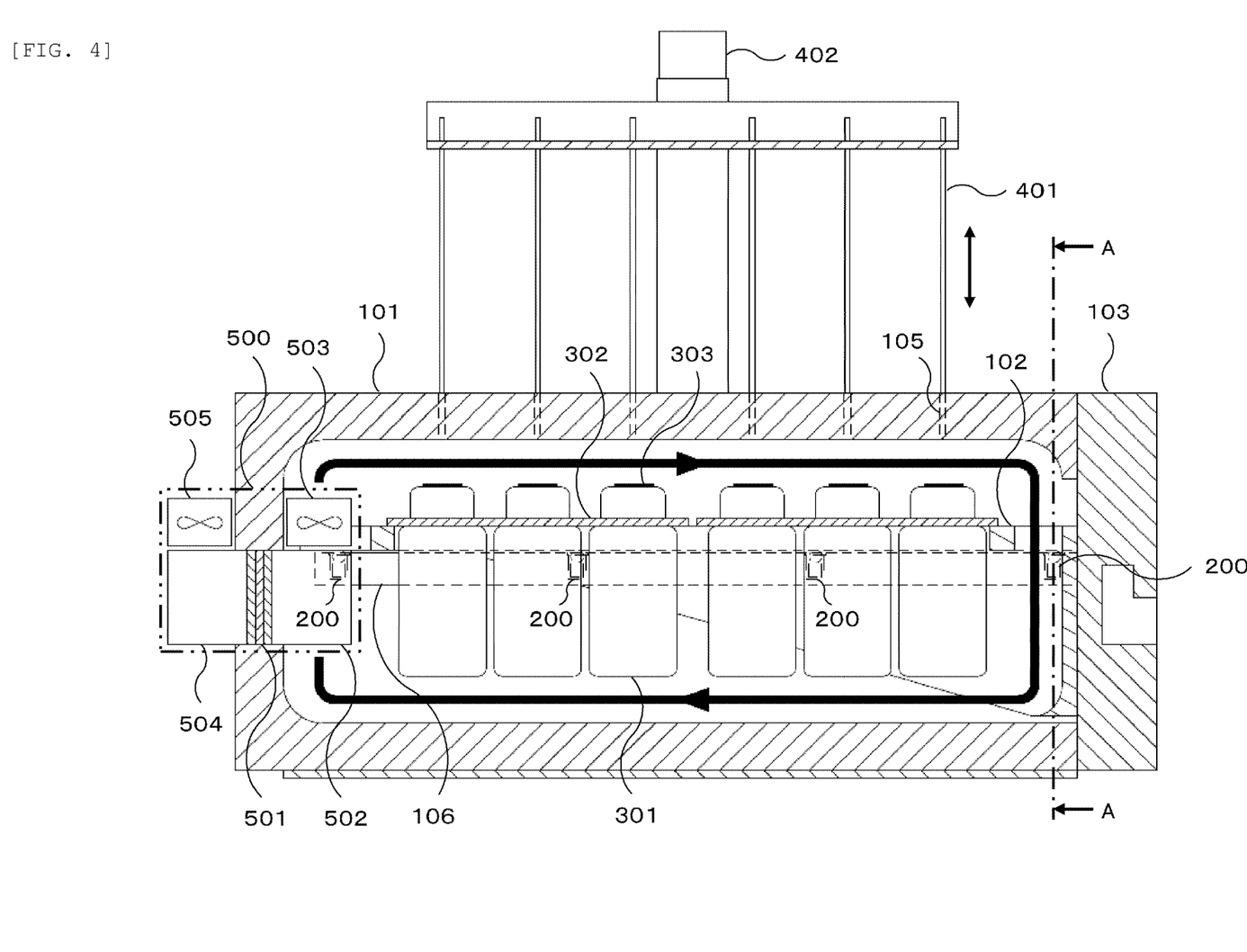
FIG. 4 is a cross-sectional view of the cooling box and the peripheral components when the drawer is closed according to the first embodiment.
Figure 5:
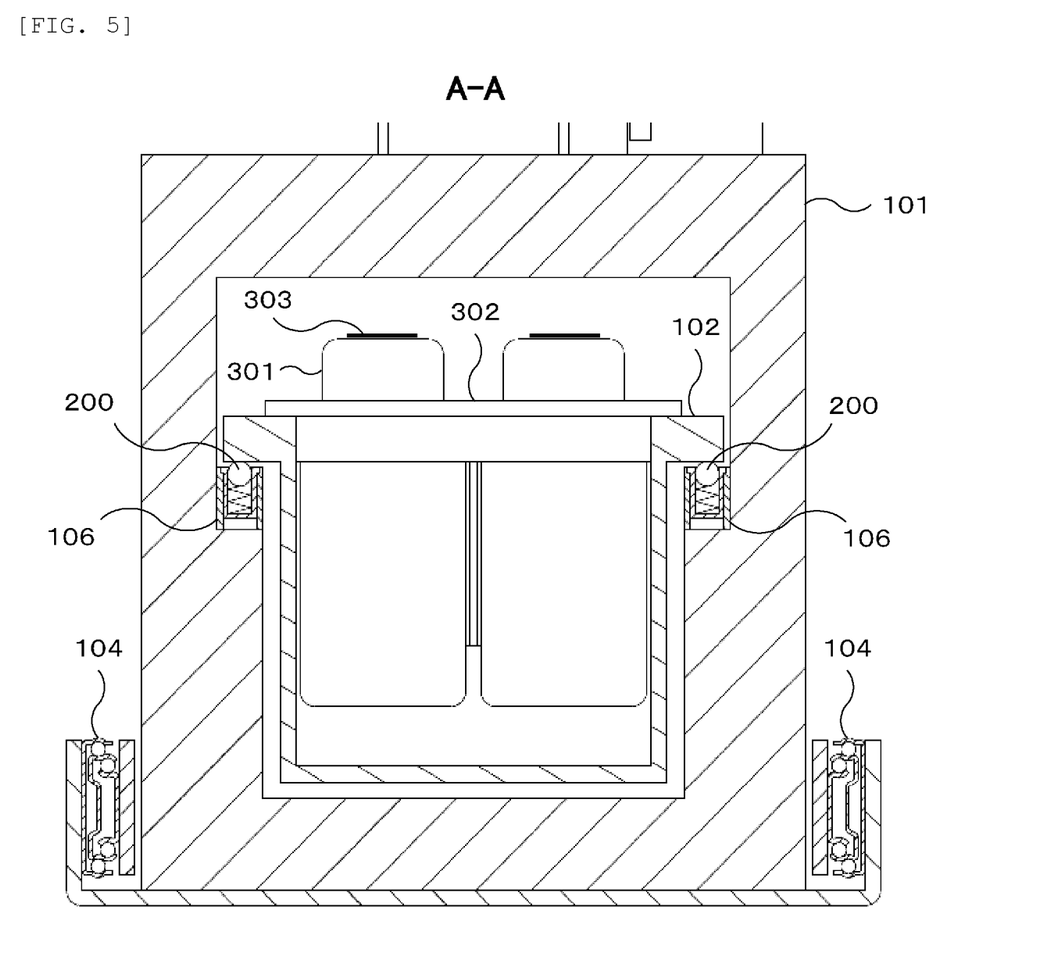
FIG. 5 is a cross-sectional view taken along a line A-A in FIG. 4.

The cooler 500 has a function of supplying cold air to the inside of the heat insulating box body 101. As shown in FIG. 4, the cooler 500 includes, as an example, a thermoelectric element 501, a cooling heat sink 502, a cooling fan 503, a heat radiation heat sink 504, and a heat radiation fan 505. The cooling heat sink 502 is cooled by the thermoelectric element 501 such as a Peltier element, and cold air is circulated to the inside of the heat insulating box body 101 by the cooling fan 503 to cool the inside of the container and keep the inside of the container in a cold state. Since an opposite side of a cooling side is heated, the heat radiation heat sink 504 and the heat radiation fan 505 for radiating the heat thereof are provided. As an example, the cooler 500 controls an inside temperature of the heat insulating box body 101 from 2° C. to 8° C.

The bridging part 102 has a function of installing the reagent containers 301. As an example, the bridging part may have a shape in which a plurality of types of reagent containers 301 can be bridged via a reagent container holder 302 having a function of collecting the reagent containers, or may have a shape in which the reagent containers 301 can be bridged one by one individually. There is a structure in which the reagent container holder 302 and the bridging part 102 are in contact with each other and the reagent container 301 is suspended. The above structure is intended to form a gap between a bottom of the reagent container 301 and an inner lower surface of the heat insulating box body 101 to secure a cold air passage. The bridging part 102 is accommodated in the heat insulating box body 101 when the drawer is closed, and is cooled together with the reagent, and thus it is desirable to reduce a heat capacity.

The drawer door 103 connects the bridging part 102 and the slide rails 104, is brought into close contact with the heat insulating box body 101 when the drawer is closed, and has a function of sealing the inside of the heat insulating box body and thermally insulating a front surface of the door. Similarly to the heat insulating box body 101, the drawer door can be formed by combining the resin material and the foamed polystyrene having the low thermal conductivity or the vacuum insulation material. It is desirable to provide a packing material on either the heat insulating box body 101 or the drawer door 103 for sealing.

The slide rail 104 has a function of smoothly opening and closing the drawer with a small force. Providing the slide rail 104 outside the cooling space of the heat insulating box body 101 can reduce the heat capacity of a cooling part. It is desirable to provide a soft closing mechanism such that the reagent does not spill over due to a force of closing the drawer.

Figure 6:
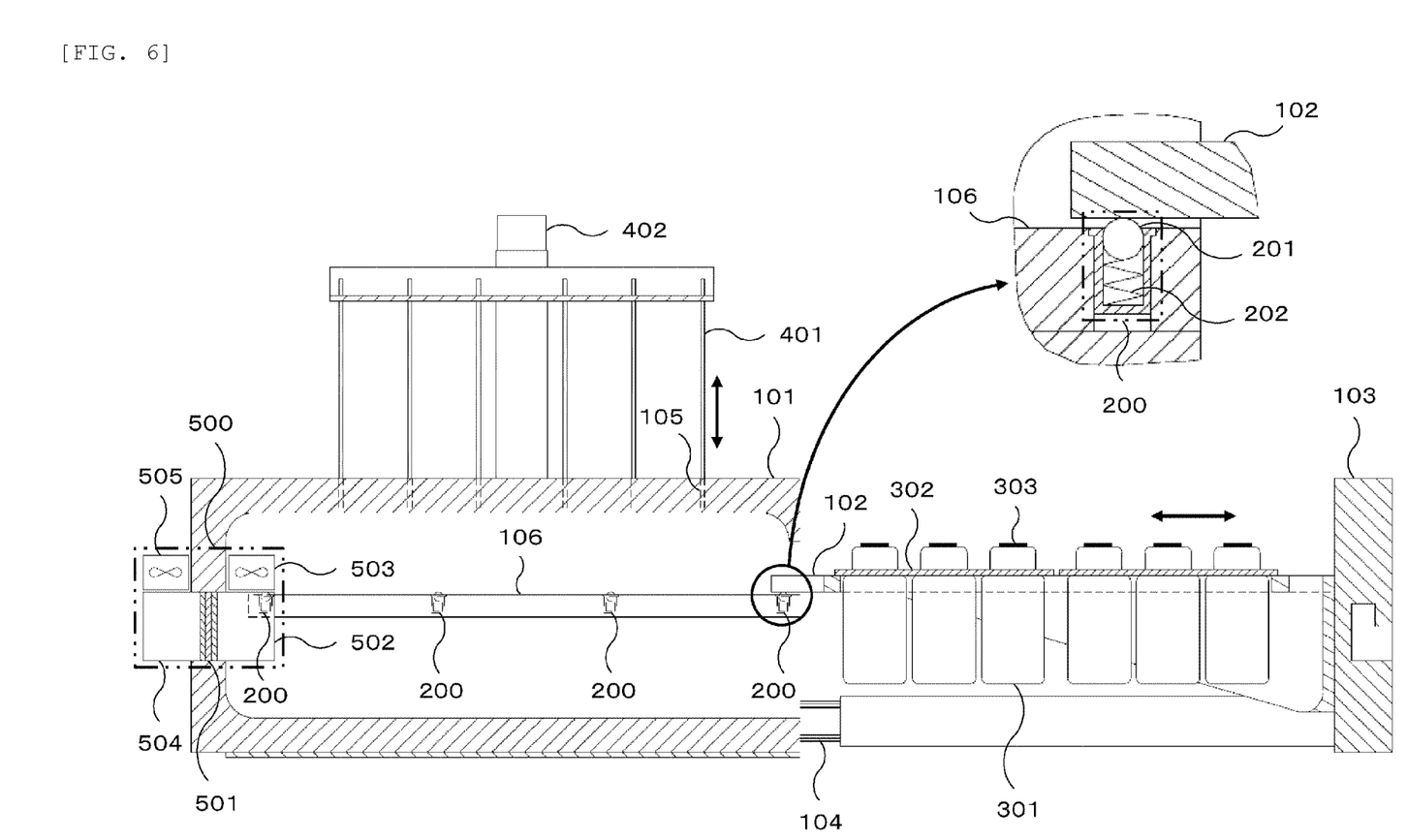
FIG. 6 is a cross-sectional view of the cooling box and the peripheral components when the drawer is open according to the first embodiment.

The heat insulating box body 101 includes a sliding member holder 106 provided with a sliding member 200. The sliding member 200 slides with the bridging part 102 at the time of opening and closing the drawer to reduce a sliding resistance. When the sliding resistance is large, there is a problem that the opening and closing of the drawer becomes heavy and that the soft closing mechanism stops halfway and the drawer is not automatically closed. Therefore, it is important to reduce the sliding resistance. The sliding member 200 includes an elastic body, and has a structure in which a sliding point moves in an upper-lower direction when a force is applied from a top to a bottom. Specifically, as shown in FIG. 6, a ball plunger including a ball 201 and a compression coil spring 202 can be used. The sliding point of the ball 201 has a structure that protrudes from an upper surface of the sliding member holder 106.

When the drawer is opened and closed in a state in which nothing is bridged on the bridging part 102 or the reagent container 301 is bridged, the bridging part 102 and the ball 201 of the sliding member 200 slide with a small resistance. When the reagent container 301 to which an aluminum film 303 is attached is mounted on the bridging part 102, the drawer is closed, the aspiration nozzle 401 is lowered from the nozzle insertion hole 105 and breaks through the aluminum film 303, a load is applied to the bridging part 102. Accordingly, the compression coil spring 202 of the sliding member 200 contracts, and the bridging part 102 and the sliding member holder 106 come into surface contact with each other. The surface contact prevents the bridging part 102 from having a cantilever structure, and has an effect of preventing deformation and breakage. No concentrated load is applied to a part of the bridging part 102 that is in contact with the sliding member 200, and thus there is an effect of preventing the deformation and the breakage similarly.

As described above, according to the present embodiment, by providing the sliding member holder provided with the sliding member including the elastic body inside the heat insulating box body, it is possible to provide a cooling box capable of preventing the deformation and the breakage of the bridging part by contacting and sliding the bridging part and the sliding member when the container is bridged on the bridging part and drawn out, and by surface contacting the bridging part and the sliding member holder when a load exceeding the weight of the bridged article is applied to the bridging part.

Second Embodiment

Figure 7:
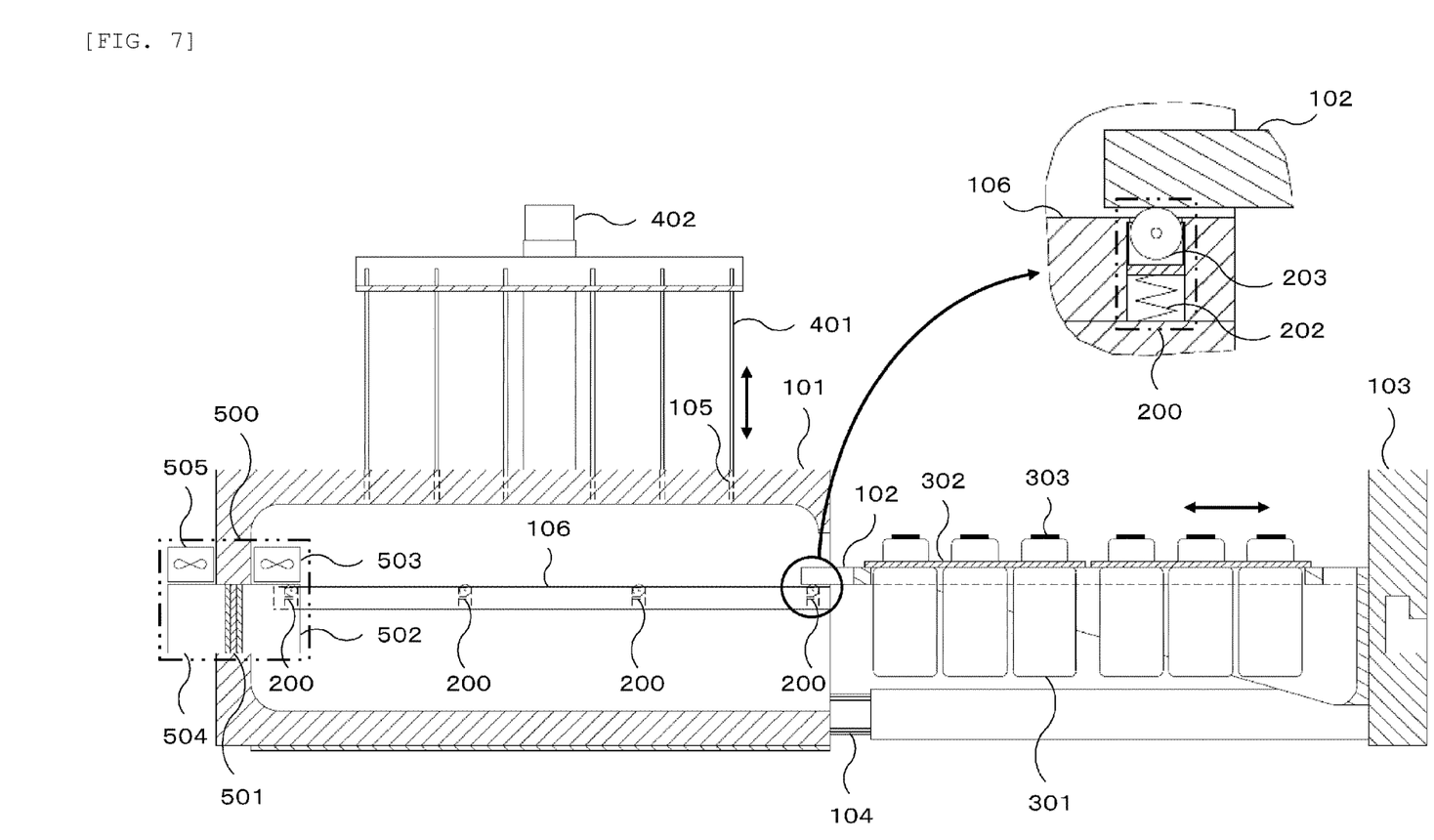
FIG. 7 is a cross-sectional view of a cooling box and peripheral components according to a second embodiment.

FIG. 7 shows the cooling box 100 according to a second embodiment. Similar to the first embodiment, the cooling box 100 according to the second embodiment includes the heat insulating box body 101, the cooler 500, the bridging part 102, the drawer door 103, and the slide rail 104, and the heat insulating box body 101 includes the nozzle insertion hole 105 and the sliding member holder 106 provided with the sliding member 200. A difference from the first embodiment is a shape of the sliding member holder 106 and a configuration of the sliding member 200. The sliding member 200 includes a roller 203 and the compression coil spring 202.

When a drawer is opened and closed in a state in which nothing is bridged on the bridging part 102 or the reagent container 301 is bridged, the bridging part 102 and the roller 203 of the sliding member 200 slide with a small resistance. When the aluminum film 303 is broken by the aspiration nozzle 401, the compression coil spring 202 of the sliding member 200 contracts, and the bridging part 102 and the sliding member holder 106 come into surface contact with each other. Therefore, there is an effect of preventing deformation and breakage of the bridging part 102.

Third Embodiment

Figure 8:
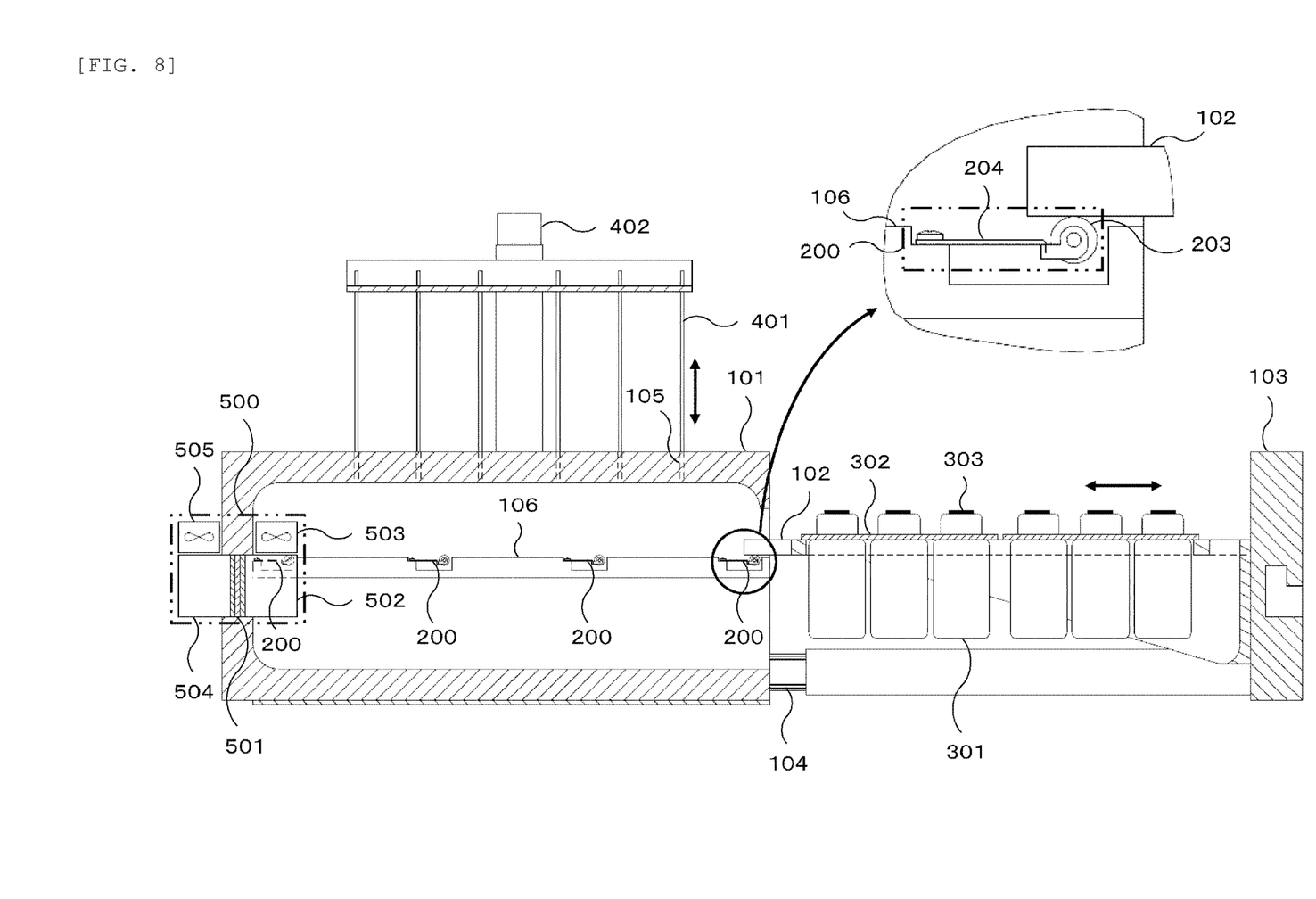
FIG. 8 is a cross-sectional view of a cooling box and peripheral components according to a third embodiment.

FIG. 8 shows a cooling box 100 according to a third embodiment. Similarly to the first embodiment and the second embodiment, the cooling box 100 according to the third embodiment includes the heat insulating box body 101, the cooler 500, the bridging part 102, the drawer door 103, and the slide rail 104, and the heat insulating box body 101 includes the nozzle insertion hole 105 and the sliding member holder 106 provided with the sliding member 200. A difference from the first embodiment and the second embodiment is a shape of the sliding member holder 106 and a configuration of the sliding member 200. The sliding member 200 includes the roller 203 and a plate spring 204.

When a drawer is opened and closed in a state in which nothing is bridged on the bridging part 102 or the reagent container 301 is bridged, the bridging part 102 and the roller 203 of the sliding member 200 slide with a small resistance. When the aluminum film 303 is broken by the aspiration nozzle 401, the plate spring 204 of the sliding member 200 is deformed, and the bridging part 102 and the sliding member holder 106 come into surface contact with each other. Therefore, there is an effect of preventing deformation and breakage of the bridging part 102.

Fourth Embodiment

Figure 9:
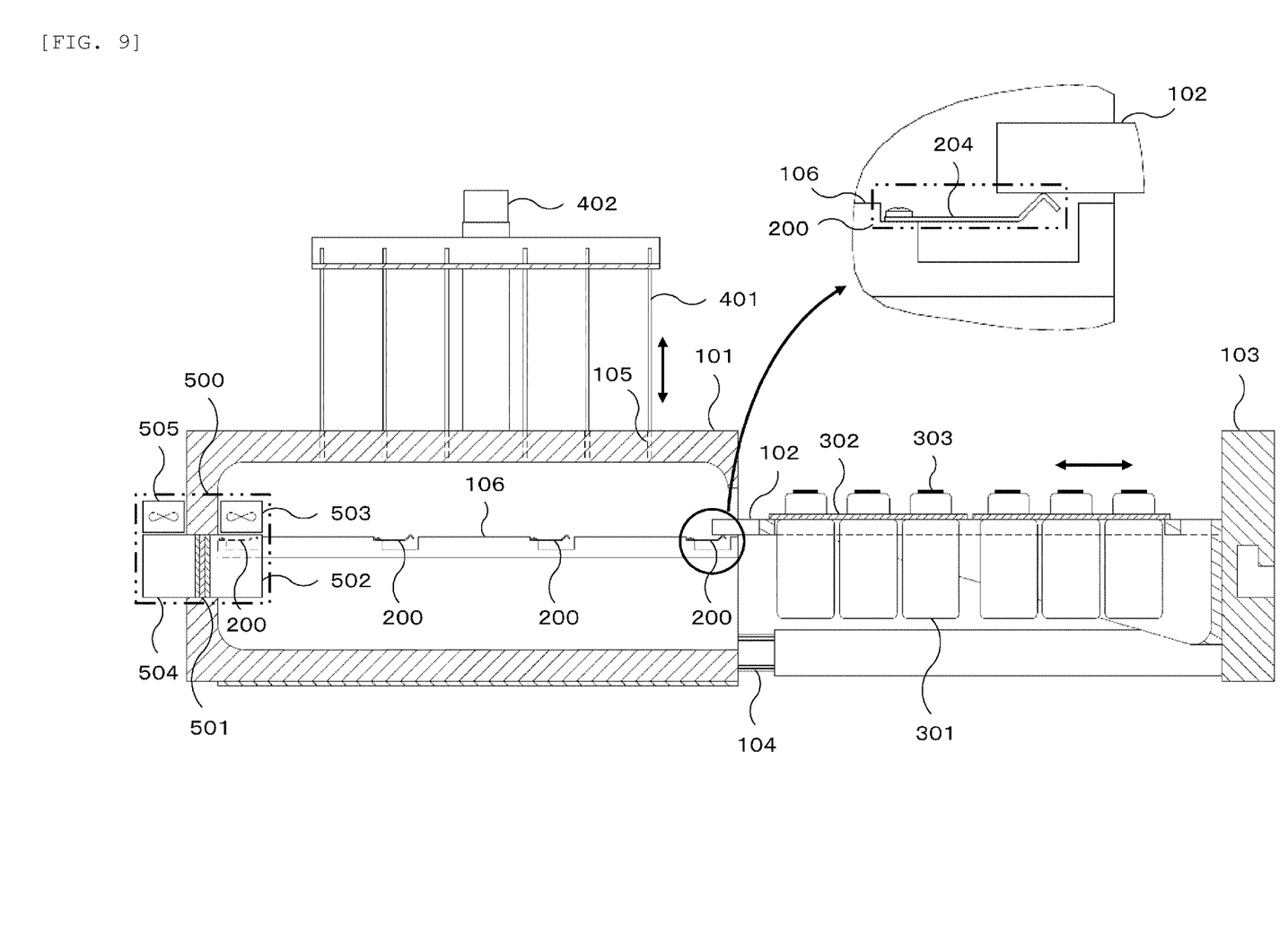
FIG. 9 is a cross-sectional view of a cooling box and peripheral components according to a fourth embodiment.

FIG. 9 shows the cooling box 100 according to a fourth embodiment. Similarly to the first embodiment to the third embodiment, the cooling box 100 according to the fourth embodiment includes the heat insulating box body 101, the cooler 500, the bridging part 102, the drawer door 103, and the slide rail 104, and the heat insulating box body 101 includes the nozzle insertion hole 105 and the sliding member holder 106 provided with the sliding member 200. A difference from the first embodiment to the third embodiment is a shape of the sliding member holder 106 and a configuration of the sliding member 200. The sliding member 200 is implemented by the plate spring 204. The plate spring 204 has a curved surface on which the plate spring slides with the bridging part 102, and reduces a sliding resistance.

When the drawer is opened and closed in which nothing is bridged on the bridging part 102 or the reagent container 301 is bridged, the bridging part 102 and the curved surface of the plate spring 204 of the sliding member 200 slide with a small resistance. When the aluminum film 303 is broken by the aspiration nozzle 401, the plate spring 204 of the sliding member 200 is deformed, and the bridging part 102 and the sliding member holder 106 come into surface contact with each other. Therefore, there is an effect of preventing deformation and breakage of the bridging part 102.

Fifth Embodiment

Figure 10:
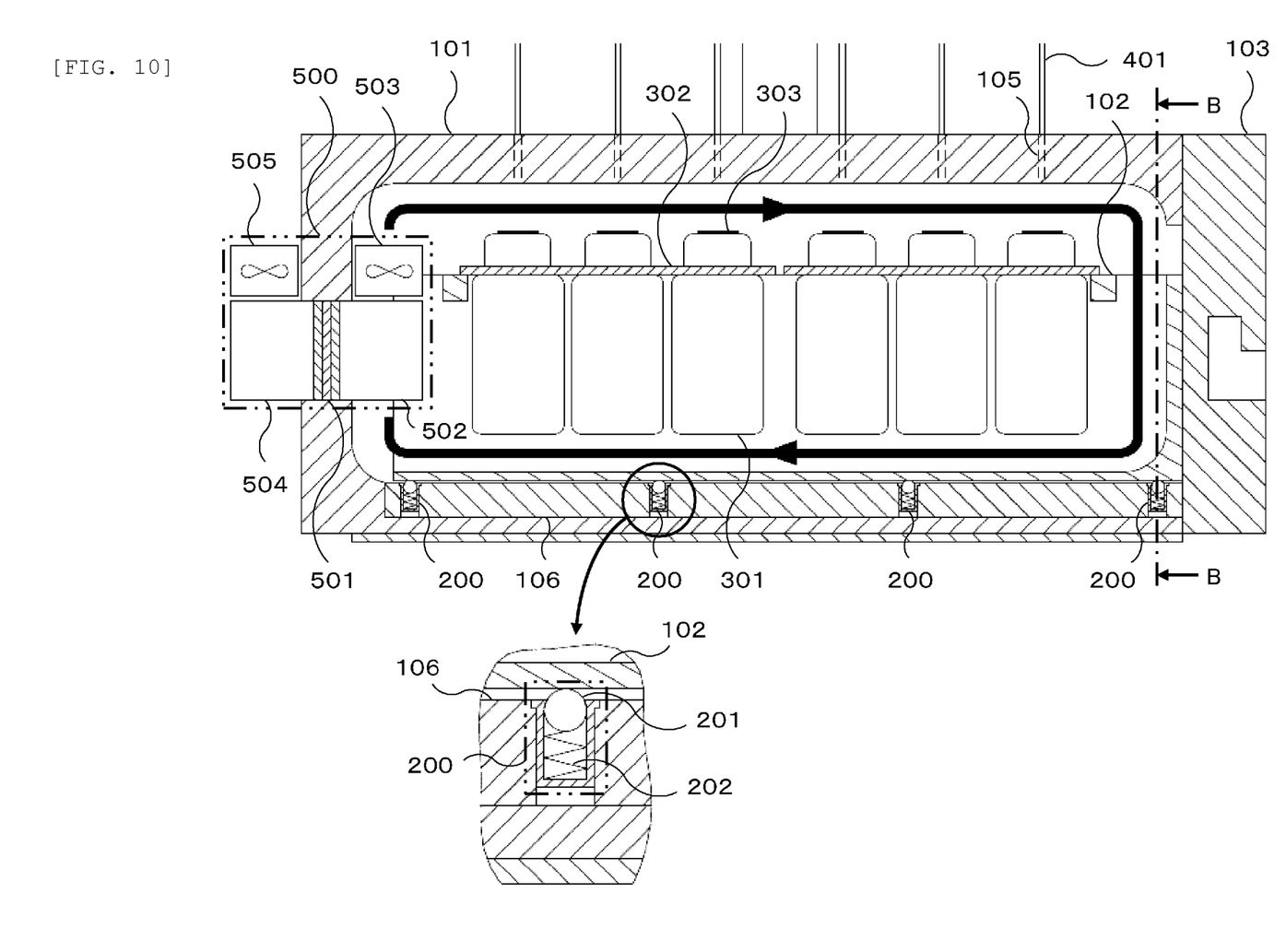
FIG. 10 is a cross-sectional view of a cooling box and peripheral components according to a fifth embodiment.
Figure 11:
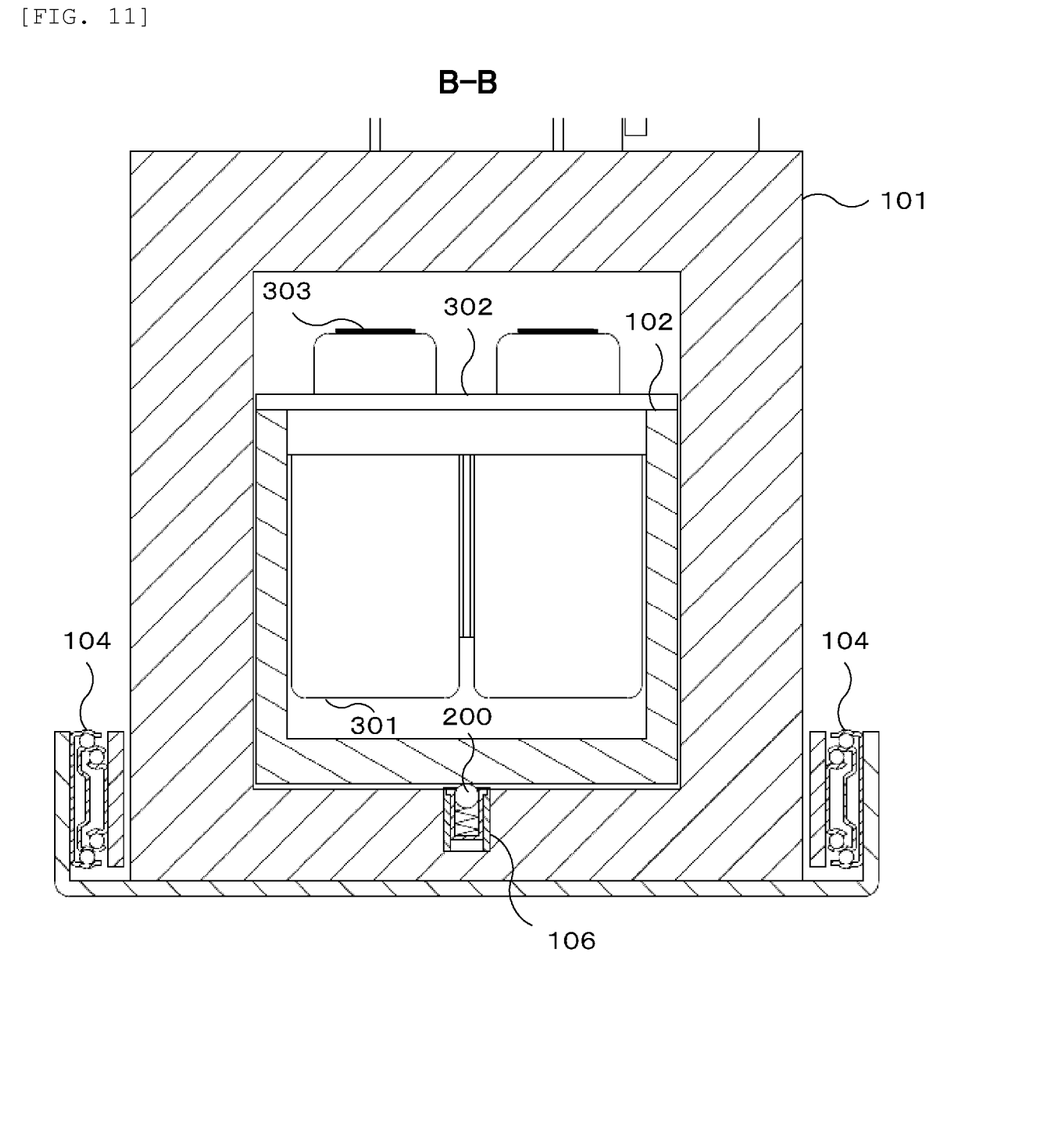
FIG. 11 is a cross-sectional view taken along a line B-B in FIG. 10.

FIGS. 10 and 11 show the cooling box 100 according to a fifth embodiment. Similarly to the first embodiment to the fourth embodiment, the cooling box 100 according to the fifth embodiment includes the heat insulating box body 101, the cooler 500, the bridging part 102, the drawer door 103, and the slide rail 104, and the heat insulating box body 101 includes the nozzle insertion hole 105 and the sliding member holder 106 provided with the sliding member 200. A difference from the first embodiment to the fourth embodiment is shapes of the heat insulating box body 101 and the bridging part 102, and disposition of the sliding member 200 and the sliding member holder 106.

In the first embodiment to the fourth embodiment, the sliding member 200 and the sliding member holder 106 are disposed on both inner side surfaces of the heat insulating box body 101. However, in the fifth embodiment, the sliding member 200 and the sliding member holder 106 are disposed on an inner lower surface of the heat insulating box body 101. Accordingly, the bridging part 102 is shaped to secure a cold air passage between the bridging part 102 and a bottom of the reagent container 301, and is shaped at the bottom to be slidable with the sliding member 200.

Sixth Embodiment

Figure 12:
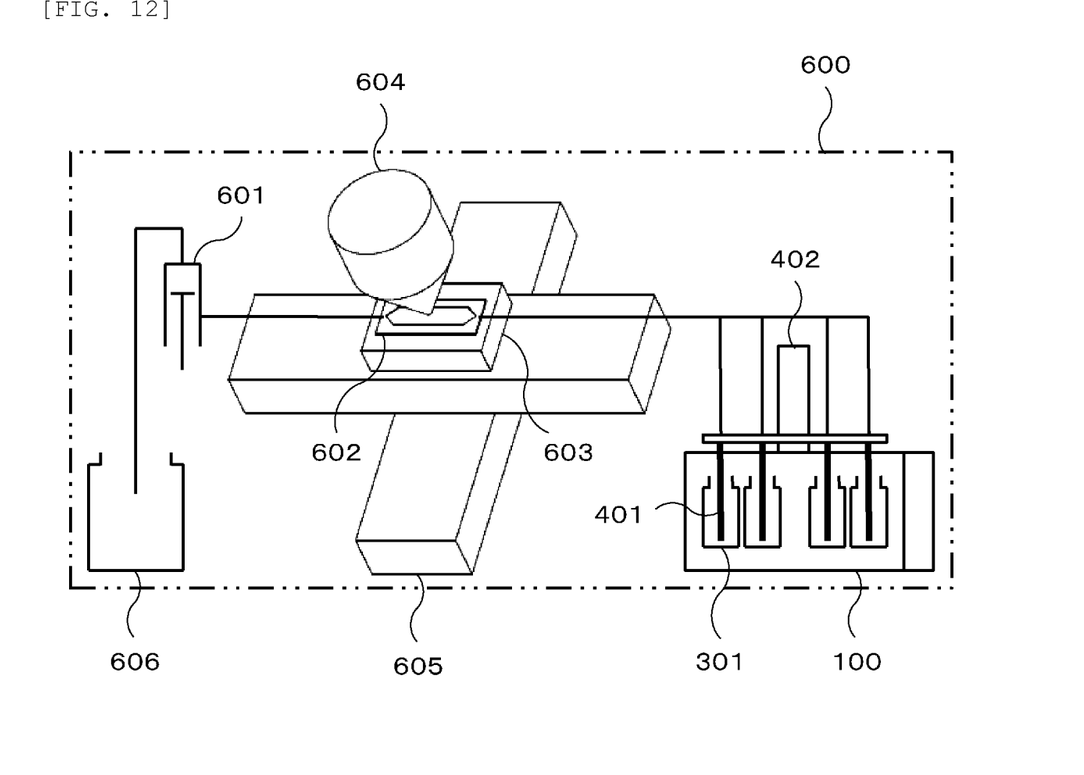
FIG. 12 is a schematic configuration diagram of a nucleic acid analysis device equipped with a cooling box in the present disclosure according to a sixth embodiment.

FIG. 12 shows a nucleic acid analysis device 600 which is an example of an analysis device equipped with the cooling box 100 according to the present disclosure. The nucleic acid analysis device 600 includes the cooling box 100, the aspiration nozzle 401, a lifting-lowering mechanism 402 that lifts and lowers the aspiration nozzle 401 to the reagent container 301 in a heat insulating box body, a liquid feeding mechanism 601 that feeds a liquid to be kept in temperature aspirated by the aspiration nozzle, a flow cell 602 disposed between the reagent container and the liquid feeding mechanism, a temperature adjusting mechanism 603 that adjusts a temperature of the flow cell, a detection unit 604 that detects inside of the flow cell, an XY stage 605, and a waste liquid tank 606.

The aspiration nozzles 401 are hollow-cylinder shaped components for aspirating a reagent contained in the reagent container 301, and the number of aspiration nozzles 401 is equal to the number of reagent containers 301.

The lifting-lowering mechanism 402 has a function of lifting and lowering a plurality of aspiration nozzles 401. When the aspiration nozzle 401 is lowered, the reagent contained in the reagent container 301 can be aspirated, and when the aspiration nozzle 401 is lifted, a drawer of the cooling box 100 can be opened and closed.

An analysis flow will be described. At the same time as a power supply of the nucleic acid analysis device 600 is turned on, cooling of the cooling box 100 is started. The drawer of the cooling box 100 is opened, and the reagent container 301 containing the reagent is provided. When the drawer of the cooling box 100 is closed, the aspiration nozzle 401 is lowered by the lifting-lowering mechanism 402. At this time, a load is applied to the drawer by breaking through the aluminum film 303 attached to an upper surface of the reagent container 301. However, deformation and breakage of the cooling box 100 do not occur according to contents of the invention described in the first embodiment to the fifth embodiment. The liquid feeding mechanism 601 feeds each reaction reagent to the flow cell 602 having a flow channel to which a DNA fragment is bound. The flow cell 602 is heated and cooled by the temperature adjusting mechanism 603 to perform an elongation reaction and to emit fluorescence. A fluorescence detection in the detection unit 604 and movement of the flow cell 602 based on the XY stage 605 are repeated to determine a base sequence. An excessive sample and a reagent after the reaction is accommodated in the waste liquid tank 606.

The present embodiment is an embodiment of the nucleic acid analysis device, and the invention can be applied to other analysis devices such as a biochemical analysis device and is not limited to the nucleic acid analysis device.

The invention is not limited to the embodiments described above and further includes various modifications. For example, the embodiments described above have been described in detail for easy understanding of the invention, and the invention is not necessarily limited to those including all configurations described above. A part of a configuration according to one embodiment can be replaced with a configuration according to another embodiment, and a configuration according to one embodiment can be added to a configuration according to another embodiment. In a part of a configuration according to each embodiment, the configuration according to another embodiment can be added, removed, or replaced.

REFERENCE SIGNS LIST

100: cooling box
101: heat insulating box body
102: bridging part
103: drawer door
104: slide rail
105: nozzle insertion hole
106: sliding member holder
200: sliding member
201: ball
202: compression coil spring
203: roller
204: plate spring
301: reagent container
302: reagent container holder
303: aluminum film
401: aspiration nozzle
402: lifting-lowering mechanism
500: cooler
501: thermoelectric element
502: cooling heat sink
503: cooling fan
504: heat radiation heat sink
505: heat radiation fan
600: nucleic acid analysis device
601: liquid feeding mechanism
602: flow cell
603: temperature adjusting mechanism
604: detection unit
605: XY stage
606: waste liquid tank

The invention claimed is:
1. A cooling box comprising:
a heat insulating box body configured to keep a temperature inside the heat insulating box body;
a cooler configured to cool inside of the heat insulating box body;
a bridging part configured to bridge a container containing a liquid to be kept in temperature to be accommodated in the heat insulating box body;
a drawer door including the bridging part; and
a slide rail that is movable in a front-rear direction, wherein
the heat insulating box body includes a nozzle insertion hole in an upper part thereof and a sliding member holder provided with a sliding member configured to slide with the bridging part, when the container is bridged on the bridging part and drawn out, the bridging part and the sliding member slide in contact with each other, and the bridging part is accommodated in the heat insulating box body, and when a load exceeding a weight of a bridged article is applied to the bridging part, the bridging part and the sliding member holder come into surface contact with each other.

2. The cooling box according to claim 1, wherein the slide rail is provided outside the heat insulating box body and is connected to the drawer door.

3. The cooling box according to claim 1, wherein the sliding member includes an elastic body.

4. The cooling box according to claim 1, wherein the sliding member is a ball plunger including a ball and a compression coil spring.

5. The cooling box according to claim 1, wherein the sliding member includes a roller and a compression coil spring.

6. The cooling box according to claim 1, wherein the sliding member includes a roller and a plate spring.

7. The cooling box according to claim 1, wherein the sliding member is implemented by a plate spring, and a sliding surface of the plate spring with respect to the bridging part is a curved surface.

8. The cooling box according to claim 1, wherein the sliding member and the sliding member holder are disposed on an inner lower surface of the heat insulating box body.

9. The cooling box according to claim 8, wherein the bridging part has a cold air passage between the bridging part and a bottom of the container.

10. An analysis device comprising:

a cooling box including an heat insulating box body configured to keep a temperature inside the heat insulating box body, a cooler configured to cool inside of the heat insulating box body, a bridging part configured to bridge a container containing a liquid to be kept in temperature to be accommodated in the heat insulating box body, a drawer door including the bridging part and a slide rail that is movable in a front-rear direction, in which, the heat insulating box body includes a nozzle insertion hole in an upper part thereof and a sliding member holder provided with a sliding member configured to slide with the bridging part, when the container is bridged on the bridging part and drawn out, the bridging part and the sliding member slide in contact with each other, and the bridging part is accommodated in the heat insulating box body, and when a load exceeding a weight of a bridged article is applied to the bridging part, the bridging part and the sliding member holder come into surface contact with each other;

a lifting-lowering mechanism configured to lift and lower an aspiration nozzle to the container in the heat insulating box body;

a liquid feeding mechanism configured to feed the liquid to be kept in temperature aspirated by the aspiration nozzle;

a flow cell provided between the container and the liquid feeding mechanism;

a temperature adjusting mechanism configured to adjust a temperature of the flow cell; and a detection unit configured to detect inside of the flow cell.

* * * * *